United States Patent
Neto et al.

(10) Patent No.: US 7,851,398 B2
(45) Date of Patent: Dec. 14, 2010

(54) CATALYTIC TITANIUM DIOXIDE MIXTURES, CATALYSTS AND CATALYST SYSTEMS CONTAINING THE SAME, PROCESSES FOR MAKING THE SAME, AND USES THEREFOR

(75) Inventors: Samuel Neto, Mannheim (DE); Sebastian Storck, Mannheim (DE); Jürgen Zühlke, Speyer (DE); Frank Rosowski, Mannheim (DE)

(73) Assignee: BASF SE, Ludwigshafen (DE)

( * ) Notice: Subject to any disclaimer, the term of this patent is extended or adjusted under 35 U.S.C. 154(b) by 23 days.

(21) Appl. No.: 11/719,422

(22) PCT Filed: Nov. 16, 2005

(86) PCT No.: PCT/EP2005/012283
§ 371 (c)(1),
(2), (4) Date: May 16, 2007

(87) PCT Pub. No.: WO2006/053732
PCT Pub. Date: May 26, 2006

(65) Prior Publication Data
US 2008/0064594 A1   Mar. 13, 2008

(30) Foreign Application Priority Data
Nov. 18, 2004 (DE) .................. 10 2004 055 807

(51) Int. Cl.
*B01J 27/198* (2006.01)
*B01J 21/06* (2006.01)

(52) U.S. Cl. .................. 502/209; 502/350; 502/353
(58) Field of Classification Search .......... None
See application file for complete search history.

(56) References Cited

U.S. PATENT DOCUMENTS

| | | | |
|---|---|---|---|
| 3,799,886 A | 3/1974 | Felice et al. | |
| 4,753,791 A | 6/1988 | Muller et al. | |
| 5,409,885 A | 4/1995 | Derian et al. | |
| 5,792,719 A | 8/1998 | Eberle et al. | |
| 5,969,160 A | 10/1999 | Lindström | |
| 6,528,683 B1 | 3/2003 | Heidemann et al. | |
| 2006/0235232 A1 | 10/2006 | Neto et al. | |
| 2006/0276661 A1 | 12/2006 | Storck et al. | |
| 2007/0060758 A1 | 3/2007 | Storck et al. | |
| 2007/0066836 A1 | 3/2007 | Neto et al. | |

FOREIGN PATENT DOCUMENTS

| | | |
|---|---|---|
| DE | 2005969 | 8/1971 |
| DE | 2106796 | 8/1972 |
| DE | 19807018 A1 | 8/1998 |
| DE | 19824532 A1 | 12/1999 |
| EP | 0063222 A2 | 10/1982 |
| EP | 522871 A1 | 1/1993 |
| EP | 539878 A2 | 5/1993 |
| EP | 744214 A1 | 11/1996 |
| EP | 985648 A1 | 3/2000 |
| WO | WO-2004103561 A1 | 12/2004 |
| WO | WO-2004103943 A1 | 12/2004 |
| WO | WO-2004103944 A1 | 12/2004 |
| WO | WO-2005011862 A1 | 2/2005 |

*Primary Examiner*—Melvin C Mayes
*Assistant Examiner*—James Corno
(74) *Attorney, Agent, or Firm*—Connolly Bove Lodge & Hutz LLP

(57) ABSTRACT

Catalytic titanium dioxide mixtures comprising: a first anatase titanium dioxide having a BET surface area greater than 15 m$^2$/g and a hydrogen uptake for the reduction of Ti$^{4+}$ to Ti$^{3+}$ of from 5 to 20 µmol/m$^2$; and a second anatase titanium dioxide having a BET surface area less than or equal to 15 m$^2$/g and a hydrogen uptake for the reduction of Ti$^{4+}$ to Ti$^{3+}$ of from 0.6 to 7 µmol/m$^2$, processes for preparing catalysts containing the same, catalysts containing active compositions including such titanium dioxide mixtures on support materials, and catalyst systems using the same.

20 Claims, No Drawings

US 7,851,398 B2

CATALYTIC TITANIUM DIOXIDE MIXTURES, CATALYSTS AND CATALYST SYSTEMS CONTAINING THE SAME, PROCESSES FOR MAKING THE SAME, AND USES THEREFOR

CROSS-REFERENCE TO RELATED APPLICATIONS

This application is a national stage application, under 35 U.S.C. §371, of PCT/EP2005/012283, filed Nov. 16, 2005, which claims priority of German Application No. 10 2004 055 807.8, filed Nov. 18, 2004.

BACKGROUND OF THE INVENTION

The present invention relates to the use of titanium dioxide mixtures in the anatase form which have defined physical properties for producing catalysts which are suitable, in particular, for the synthesis of phthalic anhydride. The invention further relates to catalysts comprising titanium dioxide mixtures in the anatase form which have defined physical properties.

Catalysts for preparing phthalic anhydride which comprise vanadium pentoxide and titanium dioxide have been known for a long time. Titanium dioxide in the anatase modification is the main constituent of the active composition of these phthalic anhydride catalysts and serves as support for the catalytically active and selective vanadium pentoxide components.

DE-A 2 106 796 describes the production of supported catalysts for the oxidation of o-xylene to phthalic anhydride, in which the titanium dioxide has a BET surface area of from 15 to 100 m$^2$/g, preferably from 25 to 50 m$^2$/g. A mixture of anatase having a BET surface area of from 7 to 11 m$^2$/g and hydrated titanium dioxide having a BET surface area of >100 m$^2$/g is particularly suitable, while the components alone would not be suitable.

EP-A 522 871 describes a relationship between the BET surface area of the titanium dioxide and the catalyst activity. According to this document, the catalyst activity is low when titanium dioxide having BET surface areas of less than 10 m$^2$/g is used. When titanium dioxide having a BET surface area of greater than 60 m$^2$/g is used, the life of the catalyst is reduced and the phthalic anhydride yield decreases sharply. Preference is given to BET surface areas of from 15 to 40 m$^2$/g.

To improve the phthalic anhydride yield and the starting behavior of the catalysts, a change has been made in recent years to the use of activity-structured catalysts. The individual catalyst zones are structured so that the activity of the individual zones generally increases from the reactor inlet to the reactor outlet.

For example, EP-A 985 648 describes the preparation of phthalic anhydride by catalytic gas-phase oxidation of o-xylene and/or naphthalene using a catalyst system which is structured so that the porosity of the catalyst and thus the activity increases pseudocontinuously from the reactor inlet to the reactor outlet. The porosity is defined as the free volume between the coated shaped bodies of the bed in the reaction tube. In the examples, the specific surface area of the active components was altered by varying the specific surface area of the titanium dioxide, which was in the range from 40 to 140 m$^2$/g.

According to the prior art summarized in EP-A1 063 222, the activity can be increased in very different ways:

(1) by means of a continual increase in the phosphorus content,
(2) by means of a continual increase in the content of active composition,
(3) by means of a continual decrease in the alkali metal content,
(4) by means of a continual decrease in the empty space between the individual catalysts,
(5) by means of a continual decrease in the content of the inert materials or
(6) by means of a continual increase in the temperature from the upper zone (reactor inlet) to the bottom zone (reactor outlet). The BET surface area of the titanium dioxide should be in the range from 10 to 60 m$^2$/g. In the examples of EP-A1 063 222, the BET surface area is constant at 22 m$^2$/g.

In multizone catalyst systems, the decrease in the activity of the first catalyst zone has an adverse effect on the life of the catalyst. With increasing aging, the conversion in the region of the first highly selective zone decreases. Over the course of the catalyst life, the main reaction zone migrates ever deeper into the catalyst bed, i.e. the o-xylene or naphthalene feed is to an increasing extent reacted only in the subsequent less selective zones. The consequences are reduced phthalic anhydride yields and an increased concentration of by-products or unreacted starting materials. To avoid migration of the main reaction zone into the subsequent zones, the salt bath temperature can be continually increased. However, as the period of operation of the catalysts increases, this measure, too, leads to a reduction in the phthalic anhydride yield.

BRIEF SUMMARY OF THE INVENTION

It was therefore an object of the invention to provide catalysts having improved properties, especially in respect of the yield. In particular, oxidation catalysts, especially phthalic anhydride catalysts, having improved activity, selectivity and yield should be provided. A further object was to find oxidation catalysts which when used in an activity-structured multizone catalyst system combine the advantages of this with those of a long life and high selectivity of the first catalyst zones.

It has surprisingly been found that titanium dioxide(s) A in the anatase modification which has/have a BET surface area of greater than 15 m$^2$/g and a hydrogen uptake for the reduction of Ti$^{4+}$ to Ti$^{3+}$ of from 5 to 20 µmol/m$^2$ in admixture with one or more further titanium dioxide(s) B in the anatase modification which has/have a BET surface area of less than or equal to 15 m$^2$/g and a hydrogen uptake for the reduction of Ti$^{4+}$ to Ti$^{3+}$ of from 0.6 to 7 µmol/m$^2$ is/are particularly suitable for producing catalysts.

It is advantageous to use titanium dioxide(s) A having a BET surface area of from 18 to 90 m$^2$/g, in particular from 18 to 55 m$^2$/g. Titanium dioxide A preferably has a hydrogen uptake for the reduction of Ti$^{4+}$ to Ti$^{3+}$ of from 5 to 17 µmol/m$^2$.

It is advantageous to use titanium dioxide(s) B having a BET surface area of from 3 to 15 m$^2$/g. Titanium dioxide B preferably has a hydrogen uptake for the reduction of Ti$^{4+}$ to Ti$^{3+}$ of from 0.6 to 5 µmol/m$^2$.

The BET surface area of the titanium dioxide mixture of A and B is advantageously in the range from 5 to 50 m$^2$/g, in particular from 10 to 30 m$^2$/g.

The mixture advantageously has a ratio of titanium dioxide(s) A to titanium dioxides (B) of from 0.5:1 to 6:1, in particular from 1:1 to 5:1.

It is advantageous to mix no more than three titanium dioxides A and no more than three titanium dioxides B with one another. The titanium dioxide mixture used according to the invention particularly preferably comprises one titanium dioxide from each of the groups A and B.

In particular, the titanium dioxide mixture used according to the invention is suitable for producing catalysts which are used in an activity-structured, at least two-zone, preferably at least three-zone, catalyst system in the uppermost catalyst zone or in the upper catalyst zones, in particular in the uppermost catalyst zone, nearest the reactor inlet.

For the purposes of the present invention, an activity-structured catalyst system is a system comprising different catalyst zones, with the activity of the catalysts changing from one zone to the next zone. In general, preference is given to catalyst systems whose activity increases essentially continuously from the reactor inlet to the reactor outlet. However, it is also possible to use one or more catalyst zones which are located upstream or in intermediate positions and have a higher activity than the subsequent zones.

DETAILED DESCRIPTION OF THE INVENTION

When the titanium dioxide mixture used according to the invention is used in a multizone catalyst system, it is advantageous to employ a ratio of titanium dioxide(s) A to titanium dioxide(s) B of from 0.8:1 to 3:1, in particular from 1:1 to 2.5:1, in the uppermost zone. Titanium dioxide mixtures or pure titanium dioxides in the anatase modification can be used in the further zones. When titanium dioxide mixtures are used, the ratio of A to B in the next lower zone is advantageously from 2:1 to 5:1.

The titanium dioxide mixture mentioned is particularly useful for producing oxidation catalysts for the synthesis of aldehydes, carboxylic acids and/or carboxylic anhydrides. In these catalytic gas-phase oxidations of aromatic or heteroaromatic hydrocarbons such as benzene, o-, m- or p-xylene, naphthalene, toluene, durene(1,2,4,5-tetramethylbenzene) or β-picoline(3-methylpyridine), products obtained are, for example, benzaldehyde, benzoic acid, maleic anhydride, phthalic anhydride, isophthalic acid, terephthalic acid, pyromellitic anhydride or nicotinic acid, depending on the starting material.

The titanium dioxide mixture mentioned is particularly useful for producing phthalic anhydride catalysts which are used in an activity-structured, at least two-zone, preferably at least three-zone, catalyst system in the uppermost catalyst zone (in a two-zone catalyst system), or in the two uppermost catalyst zones or in the uppermost catalyst zone (in a three-zone or multizone catalyst system). If appropriate, the upper catalyst zone according to the invention comprising the titanium dioxide mixture mentioned can be preceded by one or more catalyst zones.

Furthermore, it has been found that benzaldehyde, benzoic acid, maleic anhydride, phthalic anhydride, isophthalic acid, terephthalic acid, pyromellitic anhydride or nicotinic acid can be prepared advantageously using the novel catalyst described below. For this purpose, a mixture of a gas comprising molecular oxygen, for example air, and the starting material to be oxidized is generally passed through tubes in which a bed of the catalyst of the invention is located. The oxidation is particularly advantageously carried out using the catalyst of the invention in an activity-structured catalyst system.

Oxidic supported catalysts are suitable as catalysts. To prepare phthalic anhydride by gas-phase oxidation of o-xylene or naphthalene or mixtures thereof, use is usually made of spherical, annular or shell-like supports comprising a silicate, silicon carbide, porcelain, aluminum oxide, magnesium oxide, tin dioxide, rutile, aluminum silicate, magnesium silicate (steatite), zirconium silicate or cerium silicate or mixtures thereof. Coated catalysts in which the catalytically active composition has been applied in the form of a shell to the support have been found to be particularly useful. Vanadium pentoxide is preferably employed as catalytically active constituent. Furthermore, the catalytically active composition can further comprise small amounts of many other oxidic compounds which act as promoters to influence the activity and selectivity of the catalyst, for example by reducing or increasing its activity. Such promoters are, for example, the alkali metal oxides, thallium(I) oxide, aluminum oxide, zirconium oxide, iron oxide, nickel oxide, cobalt oxide, manganese oxide, tin oxide, silver oxide, copper oxide, chromium oxide, molybdenum oxide, tungsten oxide, iridium oxide, tantalum oxide, niobium oxide, arsenic oxide, antimony oxide, cerium oxide and phosphorus pentoxide. The alkali metal oxides act, for example, as promoters which reduce the activity and increase the selectivity. Furthermore, organic binders, preferably copolymers, advantageously in the form of an aqueous dispersion, of vinyl acetate/vinyl laurate, vinyl acetate/acrylate, styrene/acrylate, vinyl acetate/maleate, vinyl acetate/ethylene, and also hydroxyethylcellulose can be added to the catalytically active composition. The amounts of binder used are from 3 to 20% by weight, based on the solids content of the solution of the constituents of the active composition (EP-A 744 214). Preference is given to using organic binders as described in DE-A 198 24 532. If the catalytically active composition is applied to the support without organic binders, coating temperatures above 150° C. are advantageous. When the binders indicated above are added, usable coating temperatures are, depending on the binder used, in the range from 50 to 450° C. (DE-A 2106796). The binders applied burn out within a short time after installation of the catalyst and start-up of the reactor. The addition of binder has the advantage that the active composition adheres well to the support, so that transport and installation of the catalyst are made easier.

The catalyst for the synthesis of phthalic anhydride advantageously comprises, on a porous and/or nonporous support material, from 5 to 15% by weight, based on the total catalyst, of active composition comprising from 3 to 30% by weight of $V_2O_5$, from 0 to 4% by weight of $Sb_2O_3$, from 0 to 1.0% by weight of P, from 0 to 1.5% by weight of alkali (calculated as alkali metal) and a mixture of titanium dioxide(s) A in the anatase modification which has/have a BET surface area of greater than 15 $m^2/g$ and a hydrogen uptake for the reduction of $Ti^{4+}$ to $Ti^{3+}$ of from 5 to 20 $\mu mol/m^2$ and titanium dioxide(s) B in the anatase modification which has/have a BET surface area of less than or equal to 15 $m^2/g$ and a hydrogen uptake for the reduction of $Ti^{4+}$ to $Ti^{3+}$ of from 0.6 to 7 $\mu mol/m^2$ as balance.

In a preferred embodiment, the catalyst in the first, uppermost zone comprises, on support material, from 5 to 12% by weight, based on the total catalyst, of active composition comprising from 3 to 20% by weight of $V_2O_5$, from 0 to 4% by weight of $Sb_2O_3$, from 0 to 0.5% by weight of P, from 0.1 to 1.5% by weight of alkali (calculated as alkali metal) and a mixture of titanium dioxide(s) A in the anatase modification which has/have a BET surface area of greater than 15 $m^2/g$ and a hydrogen uptake for the reduction of $Ti^{4+}$ to $Ti^{3+}$ of from 5 to 20 $\mu mol/m^2$ and titanium dioxide(s) B in the anatase modification which has/have a BET surface area of less than or equal to 15 $m^2/g$ and a hydrogen uptake for the reduction of $Ti^{4+}$ to $Ti^{3+}$ of from 0.6 to 7 $\mu mol/m^2$ as balance.

It is usual to employ multizone catalyst systems in which the less active catalyst is arranged in the fixed bed so that the reaction gas comes into contact with this catalyst first and only subsequently comes into contact with the more active catalyst in the second zone. If appropriate, catalyst zones which are located upstream or in intermediate positions and have a higher activity than the subsequent catalyst zone can be used. The reaction gas then comes into contact with the even more active catalyst zones. The catalysts of differing activity can be thermostated to the same temperature or to different temperatures.

Preference is given to using three- to five-zone catalyst systems, in particular three- and four-zone catalyst systems. Particular preference is given to catalyst systems whose catalyst activity increases essentially continuously from zone to zone.

In a preferred embodiment of an at least three-zone catalyst system, the catalysts for the synthesis of phthalic anhydride have the following composition:

for the first, uppermost zone (zone a) nearest the reactor inlet):
from 7 to 10% by weight, based on the total catalyst, of active composition comprising:
from 6 to 11% by weight of vanadium (calculated as $V_2O_5$)
from 0 to 3% by weight of antimony trioxide
from 0.1 to 1% by weight of an alkali (calculated as alkali metal), in particular cesium oxide,
and, as balance to 100% by weight, a mixture of titanium dioxide(s) A in the anatase modification which has/have a BET surface area of greater than 15 $m^2/g$ and a hydrogen uptake for the reduction of $Ti^{4+}$ to $Ti^{3+}$ of from 5 to 20 $\mu mol/m^2$ and titanium dioxide(s) B in the anatase modification which has/have a BET surface area of less than or equal to 15 $m^2/g$ and a hydrogen uptake for the reduction of $Ti^{4+}$ to $Ti^{3+}$ of from 0.6 to 7 $\mu mol/m^2$ for the second, middle zone (zone b)):
from 7 to 12% by weight, based on the total catalyst, of active composition comprising:
from 5 to 13% by weight of vanadium (calculated as $V_2O_5$)
from 0 to 3% by weight of antimony trioxide
from 0 to 0.4% by weight of an alkali (calculated as alkali metal), in particular cesium oxide,
from 0 to 0.4% by weight of phosphorus pentoxide (calculated as P)
and, as balance to 100% by weight titanium dioxide in the anatase modification, if appropriate as in zone a)

for the third, bottommost zone (zone c) nearest the reactor outlet):
from 8 to 12% by weight, based on the total catalyst, of active composition comprising:
from 5 to 30% by weight of vanadium (calculated as $V_2O_5$)
from 0 to 3% by weight of antimony trioxide
from 0 to 0.3% by weight an alkali (calculated as alkali metal), in particular cesium oxide
from 0.05 to 0.4% by weight of phosphorus pentoxide (calculated as P)
and, as balance to 100% by weight titanium dioxide, in particular in the anatase modification, if appropriate as in zone a).

In a preferred embodiment of an at least four-zone catalyst system, the catalysts have the following composition:

for the first zone (zone a) nearest the reactor inlet):
from 7 to 10% by weight, based on the total catalyst, of active composition comprising:
from 6 to 11% by weight of vanadium (calculated as $V_2O_5$)
from 0 to 3% by weight of antimony trioxide
from 0.1 to 1% by weight of an alkali (calculated as alkali metal), in particular cesium oxide,
and, as balance to 100% by weight, a mixture of titanium dioxide(s) A in the anatase modification which has/have a BET surface area of greater than 15 $m^2/g$ and a hydrogen uptake for the reduction of $Ti^{4+}$ to $Ti^{3+}$ of from 5 to 20 $\mu mol/m^2$ and titanium dioxide(s) B in the anatase modification which has/have a BET surface area of less than or equal to 15 $m^2/g$ and a hydrogen uptake for the reduction of $Ti^{4+}$ to $Ti^{3+}$ of from 0.6 to 7 $\mu mol/m^2$ for the second zone (zone b1)):
from 7 to 12% by weight, based on the total catalyst, of active composition comprising:
from 4 to 15% by weight of vanadium (calculated as $V_2O_5$)
from 0 to 3% by weight of antimony trioxide
from 0.1 to 1% by weight of an alkali (calculated as alkali metal), in particular cesium oxide
from 0 to 0.4% by weight of phosphorus pentoxide (calculated as P)
and, as balance to 100% by weight, titanium dioxide in the anatase modification, if appropriate as in zone a)

for the third zone (zone b2)):
from 7 to 12% by weight, based on the total catalyst, of active composition comprising:
from 5 to 15% by weight of vanadium (calculated as $V_2O_5$)
from 0 to 3% by weight of antimony trioxide
from 0 to 0.4% by weight of an alkali (calculated as alkali metal), in particular cesium oxide
from 0 to 0.4% by weight of phosphorus pentoxide (calculated as P)
and, as balance to 100% by weight, titanium dioxide in the anatase modification, if appropriate as in zone a)

for the fourth zone (zone c) nearest the reactor outlet):
from 8 to 12% by weight, based on the total catalyst, of active composition comprising:
from 5 to 30% by weight of vanadium (calculated as $V_2O_5$)
from 0 to 3% by weight of antimony trioxide
from 0.05 to 0.4% by weight of phosphorus pentoxide (calculated as P)
and, as balance to 100% by weight, titanium dioxide in the anatase modification, if appropriate as in zone a).

In general, the catalyst zones a), b1), b2) and/or c) can also each consist of two or more zones. These intermediate zones advantageously have intermediate catalyst compositions.

Instead of mutually delineated zones of the various catalysts, it is also possible for a pseudocontinuous transition of the zones and an effectively uniform increase in the activity to be obtained by provision of a zone comprising a mixture of the successive catalysts at the transition from one zone to the next zone.

To carry out the reaction, the catalysts are introduced zone-wise into the tubes of a shell-and-tube reactor. The reaction gas is passed over the catalyst bed obtained in this way at salt bath temperatures of generally from 300 to 450° C., preferably from 320 to 420° C. and particularly preferably from 340 to 400° C. The various catalyst beds can, however, also be thermostated to different temperatures.

The bed length of the first catalyst zone preferably makes up from >20 to 80% of the total catalyst fill height in the reactor. The bed height of the first two or the first three catalyst zones advantageously makes up from >60 to 95% of the total catalyst fill height. If appropriate, one or more catalyst zones which preferably make up less than 20% of the total catalyst fill height can be located upstream of the abovementioned first catalyst zone. Typical reactors have a fill height of from 250 cm to 350 cm. The catalyst zones can also, if appropriate, be distributed over a plurality of reactors.

The reaction gas fed to the catalyst (starting gas mixture) is generally produced by mixing a gas which comprises molecular oxygen and can further comprise, in addition to oxygen, suitable reaction moderators such as nitrogen and/or diluents such as steam and/or carbon dioxide with the o-xylene or naphthalene to be oxidized. The reaction gas generally comprises from 1 to 100 mol %, preferably from 2 to 50 mol % and particularly preferably from 10 to 30 mol %, of oxygen. In general, the reaction gas is laden with from 5 to 140 g, preferably from 60 to 120 g and particularly preferably from 80 to 120 g, of o-xylene and/or naphthalene per standard $m^3$ of gas.

If desired, a downstream finishing reactor as described, for example, in DE-A 198 07 018 or DE-A 20 05 969 can also be provided for the preparation of phthalic anhydride. The catalyst used here is preferably a catalyst which is even more active than the catalyst of the last zone.

The catalysts of the invention have the advantage of improved performance. This improvement is also found at high loadings with o-xylene and/or naphthalene, e.g. 100 g/standard $m^3$.

EXAMPLES

A. Production of the Catalysts

A.1 Production of the Catalyst System 1 According to the Invention (4-Zone Catalyst System)

Upper Zone (a)

29.3 g of anatase (BET SA: 7 $m^2$/g, $H_2$ uptake: 4.9 µmol/$m^2$), 69.8 g of anatase (BET SA: 20 $m^2$/g, $H_2$ uptake: 7.7 µmol/$m^2$), 7.8 g of $V_2O_5$, 1.9 g of $Sb_2O_3$, 0.49 g of $Cs_2CO_3$ were suspended in 550 ml of deionized water and stirred for 18 hours. 50 g of organic binder comprising a copolymer of vinyl acetate and vinyl laurate in the form of a 50% strength by weight aqueous dispersion were added to this suspension. The suspension obtained was subsequently sprayed onto 1200 g of steatite (magnesium silicate) in the form of rings having an external diameter of 7 mm, a length of 7 mm and a wall thickness of 1.5 mm and dried. The weight of the shell applied was 8% of the total weight of the finished catalyst.

The catalytically active composition applied in this way comprised 7.1% by weight of vanadium (calculated as $V_2O_5$), 1.8% by weight of antimony (calculated as $Sb_2O_3$), 0.36% by weight of cesium (calculated as Cs) after calcination at 450° C. for one hour. The BET surface area of the $TiO_2$ mixture was 15.8 $m^2$/g.

Upper Middle Zone (b1)

24.6 g of anatase (BET SA: 7 $m^2$/g, $H_2$ uptake: 4.9 µmol/$m^2$), 74.5 g of anatase (BET SA: 20 $m^2$/g, $H_2$ uptake: 7.7 µmol/$m^2$), 7.8 g of $V_2O_5$, 2.6 g of $Sb_2O_3$, 0.35 g of $Cs_2CO_3$ were suspended in 550 ml of deionized water and stirred for 18 hours. 50 g of organic binder comprising a copolymer of vinyl acetate and vinyl laurate in the form of a 50% strength by weight aqueous dispersion were added to this suspension. The suspension obtained was subsequently sprayed onto 1200 g of steatite (magnesium silicate) in the form of rings having an external diameter of 7 mm, a length of 7 mm and a wall thickness of 1.5 mm and dried. The weight of the shell applied was 8% of the total weight of the finished catalyst.

The catalytically active composition applied in this way, i.e. the catalyst shell, comprised 7.1% by weight of vanadium (calculated as $V_2O_5$), 2.4% by weight of antimony (calculated as $Sb_2O_3$), 0.26% by weight of cesium (calculated as Cs) after calcination at 450° C. for one hour. The BET surface area of the $TiO_2$ mixture was 16.4 $m^2$/g.

Lower Middle Zone (b2)

24.8 g of anatase (BET SA: 7 $m^2$/g, $H_2$ uptake: 4.9 µmol/$m^2$), 74.5 g of anatase (BET SA: 20 $m^2$/g, $H_2$ uptake: 7.7 µmol/$m^2$), 7.8 g of $V_2O_5$, 2.6 g of $Sb_2O_3$, 0.13 g of $Cs_2CO_3$ were suspended in 550 ml of deionized water and stirred for 18 hours. 50 g of organic binder comprising a copolymer of vinyl acetate and vinyl laurate in the form of a 50% strength by weight aqueous dispersion were added to this suspension. The suspension obtained was subsequently sprayed onto 1200 g of steatite (magnesium silicate) in the form of rings having an external diameter of 7 mm, a length of 7 mm and a wall thickness of 1.5 mm and dried. The weight of the shell applied was 8% of the total weight of the finished catalyst.

The catalytically active composition applied in this way, i.e. the catalyst shell, comprised 7.1% by weight of vanadium (calculated as $V_2O_5$), 2.4% by weight of antimony (calculated as $Sb_2O_3$), 0.10% by weight of cesium (calculated as Cs) after calcination at 450° C. for one hour. The BET surface area of the $TiO_2$ mixture was 16.4 $m^2$/g.

Bottom Zone (c)

17.2 g of anatase (BET SA: 7 $m^2$/g, $H_2$ uptake: 4.9 µmol/$m^2$), 69.1 g of anatase (BET SA: 27 $m^2$/g, $H_2$ uptake: 16.1 µmol/$m^2$), 21.9 g of $V_2O_5$, 1.5 g of $NH_4H_2PO_4$ were suspended in 550 ml of deionized water and stirred for 18 hours. 55 g of organic binder comprising a copolymer of vinyl acetate and vinyl laurate in the form of a 50% strength by weight aqueous dispersion were added to this suspension. The suspension obtained was subsequently sprayed onto 1200 g of steatite (magnesium silicate) in the form of rings having an external diameter of 7 mm, a length of 7 mm and a wall thickness of 1.5 mm and dried. The weight of the shell applied was 8% of the total weight of the finished catalyst.

The catalytically active composition applied in this way, i.e. the catalyst shell, comprised 20.00% by weight of vanadium (calculated as $V_2O_5$), 0.38% by weight of phosphorus (calculated as P) after calcination at 450° C. for one hour. The BET surface area of the $TiO_2$ mixture was 20.9 $m^2$/g.

A.2 Production of the Catalyst System 2 According to the Invention (3-Zone Catalyst System)

Upper Zone (a)

34.3 g of anatase (BET SA: 7 $m^2$/g, $H_2$ uptake: 4.9 µmol/$m^2$), 63.6 g of anatase (BET SA: 20 $m^2$/g, $H_2$ uptake: 7.7 µmol/$m^2$), 7.74 g of $V_2O_5$, 2.58 g of $Sb_2O_3$, 0.48 g of $Cs_2CO_3$ were suspended in 650 ml of deionized water and stirred for 15 hours. 50 g of an aqueous dispersion (50% by weight) of vinyl acetate and vinyl laurate were subsequently added to this suspension. The suspension was subsequently applied to 1200 g of shaped steatite bodies (magnesium silicate) in the form of rings (7×7×4 mm, ED×L×ID) by spraying. The weight of the shell of active composition applied was 8% of the total weight of the finished catalyst.

The catalytically active composition applied in this way comprised 7.1% by weight of $V_2O_5$, 2.4% by weight of $Sb_2O_3$, 0.36% by weight of Cs after calcination at 400° C. for 4 hours. The BET surface area was 14.7 $m^2$/g.

Middle Zone (b)

24.6 g of anatase (BET SA: 7 $m^2$/g, $H_2$ uptake: 4.9 µmol/$m^2$), 54.9 g of anatase (BET SA: 27 $m^2$/g, $H_2$ uptake: 16.1 µmol/$m^2$), 7.74 g of $V_2O_5$, 2.37 g of $Sb_2O_3$, 0.10 g of $Cs_2CO_3$ were suspended in 650 ml of deionized water and stirred for 15 hours. 55 g of an aqueous dispersion (50% by weight) of vinyl acetate and vinyl laurate were subsequently added to this suspension The suspension was subsequently applied to 1200 g of shaped steatite bodies (magnesium silicate) in the form of rings (7×7×4 mm, ED×L×ID) by spraying. The weight of the shell of active composition applied was 9% of the total weight of the finished catalyst.

The catalytically active composition applied in this way comprised 8.6% by weight of $V_2O_5$, 2.6% by weight of $Sb_2O_3$, 0.10% by weight of Cs after calcination at 400° C. for 4 hours. The BET surface area was 20.8 $m^2/g$.

Bottom Zone (c)

24.6 9 of anatase (BET SA: 7 $m^2/g$, $H_2$ uptake: 4.9 μmol/$m^2$), 73.7 g of anatase (BET SA: 30 $m^2/g$, $H_2$ uptake: 2.8 μmol/$m^2$), 25.0 g of $V_2O_5$, 1.7 g of $NH_4H_2PO_4$ were suspended in 650 ml of deionized water and stirred for 15 hours. 62 g of an aqueous dispersion (50% by weight) of vinyl acetate and vinyl laurate were subsequently added to this suspension. The suspension was subsequently applied to 1200 g of shaped steatite bodies (magnesium silicate) in the form of rings (7×7×4 mm, ED×L×ID) by spraying. The weight of the shell of active composition applied was 10% of the total weight of the finished catalyst.

The catalytically active composition applied in this way comprised 20.0% by weight of $V_2O_5$, 0.4% by weight of P after calcination at 400° C. for 4 hours. The BET surface area was 24.2 $m^2/g$.

A.3 Production of the Comparative Catalyst System 3 (3-Zone Catalyst System)

Upper Zone (a)

46.0 g of anatase (BET SA: 9 $m^2/g$, $H_2$ uptake: 0.4 μmol/$m^2$), 51.9 g of anatase (BET SA: 27 $m^2g$, $H_2$ uptake: 16.1 μmol/$m^2$), 7.74 g of $V_2O_5$, 2.58 g of $Sb_2O_3$, 0.44 g of $Cs_2CO_3$ were suspended in 650 ml of deionized water and stirred for 15 hours. 50 g of an aqueous dispersion (50% by weight) of vinyl acetate and vinyl laurate were subsequently added to this suspension. The suspension was subsequently applied to 1200 g of shaped steatite bodies (magnesium silicate) in the form of rings (7×7×4 mm, external diameter (ED)×length (L)×internal diameter (ID)) by spraying. The weight of the shell of active composition applied was 8% of the total weight of the finished catalyst.

The catalytically active composition applied in this way comprised 7.1% by weight of $V_2O_5$, 2.4% by weight of $Sb_2O_3$, 0.33% by weight of Cs after calcination at 400° C. for 4 hours. The BET surface area was 18.4 $m^2/g$.

Middle Zone (b)

21.5 g of anatase (BET SA: 9 $m^2/g$, $H_2$ uptake: 0.4 μmol/$m^2$), 86.1 g of anatase (BET SA: 27 $m^2/g$, $H_2$ uptake: 16.1 μmol/$m^2$), 14.2 g of $V_2O_5$, 1.7 g of $NH_4H_2PO_4$ were suspended in 550 ml of deionized water and stirred for 15 hours. 55 g of an aqueous dispersion (50% by weight) of vinyl acetate and vinyl laurate were subsequently added to this suspension. The suspension was subsequently applied to 1200 g of shaped steatite bodies (magnesium silicate) in the form of rings (7×7×4 mm, ED×L×ID) by spraying. The weight of the shell of active composition applied was 9% of the total weight of the finished catalyst.

The catalytically active composition applied in this way comprised 11.5% by weight of $V_2O_5$, 0.4% by weight of P after calcination at 400° C. for 4 hours. The BET surface area was 21.3 $m^2/g$.

Bottom Zone (c)

24.6 g of anatase (BET SA: 9 $m^2/g$, $H_2$ uptake: 0.4 μmol/$m^2$), 73.7 g of anatase (BET SA: 30 $m^2/g$, $H_2$ uptake: 2.8 μmol/$m^2$), 25.0 g of $V_2O_5$, 1.7 g of $NH_4H_2PO_4$ were suspended in 550 ml of deionized water and stirred for 15 hours. 62 g of an aqueous dispersion (50% by weight) of vinyl acetate and vinyl laurate were subsequently added to this suspension. The suspension was subsequently applied to 1200 g of shaped steatite bodies (magnesium silicate) in the form of rings (7×7×4 mm, ED×L×ID) by spraying. The weight of the shell of active composition applied was 9% of the total weight of the finished catalyst.

The catalytically active composition applied in this way comprised 20.0% by weight of $V_2O_5$, 0.4% by weight of P after calcination at 400° C. for 4 hours. The BET surface area was 19.9 $m^2/g$.

A.4 Production of the Comparative Catalyst System 4 (3-Zone Catalyst System)

Upper Zone (a)

34.3 g of anatase (BET SA: 9 $m^2/g$, $H_2$ uptake: 0.4 μmol/$m^2$), 63.6 g of anatase (BET SA: 20 $m^2/g$, $H_2$ uptake: 1.5 μmol/$m^2$), 7.74 g of $V_2O_5$, 2.58 g of $Sb_2O_3$, 0.48 g of $Cs_2CO_3$ were suspended in 650 ml of deionized water and stirred for 15 hours. 50 g of an aqueous dispersion (50% by weight) of vinyl acetate and vinyl laurate were subsequently added to this suspension. The suspension was subsequently applied to 1200 g of shaped steatite bodies (magnesium silicate) in the form of rings (7×7×4 mm, ED×L×ID) by spraying. The weight of the shell of active composition applied was 8% of the total weight of the finished catalyst.

The catalytically active composition applied in this way comprised 7.1% by weight of $V_2O_5$, 2.4% by weight of $Sb_2O_3$, 0.36% by weight of Cs after calcination at 400° C. for 4 hours. The BET surface area was 16.1 $m^2/g$.

Middle Zone (b)

34.3 g of anatase (BET SA: 9 $m^2/g$, $H_2$ uptake: 0.4 μmol/$m^2$), 102.9 g of anatase (BET SA: 20 $m^2/g$, $H_2$ uptake: 1.5 μmol/$m^2$), 11.0 g of $V_2O_5$, 3.7 g of $Sb_2O_3$, 2.3 g of $NH_4H_2PO_4$ and 0.19 g of $Cs_2CO_3$ were suspended in 650 ml of deionized water and stirred for 15 hours. 52 g of an aqueous dispersion (50% by weight) of vinyl acetate and vinyl laurate were subsequently added to this suspension. The suspension was subsequently applied to 1200 g of shaped steatite bodies (magnesium silicate) in the form of rings (7×7×4 mm, ED×L×ID) by spraying. The weight of the shell of active composition applied was 9% of the total weight of the finished catalyst. The catalytically active composition applied in this way comprised 7.1% by weight of $V_2O_5$, 2.4% by weight of $Sb_2O_3$, 0.10% by weight of Cs, 0.4% by weight of P after calcination at 400° C. for 4 hours. The BET surface area was 17.3 $m^2/g$.

Bottom Zone (c)

28.7 g of anatase (BET SA: 9 $m^2/g$, $H_2$ uptake: 0.4 μmol/$m^2$), 86.2 g of anatase (BET SA: 30 $m^2/g$, $H_2$ uptake: 2.8 μmol/$m^2$), 29.2 g of $V_2O_5$, 2.0 g of $NH_4H_2PO_4$ were suspended in 650 ml of deionized water and stirred for 15 hours. 60 g of an aqueous dispersion (50% by weight) of vinyl acetate and vinyl laurate were subsequently added to this suspension. The suspension was subsequently applied to 1200 g of shaped steatite bodies (magnesium silicate) in the form of rings (7×7×4 mm, ED×L×ID) by spraying. The weight of the shell of active composition applied was 10% of the total weight of the finished catalyst.

The catalytically active composition applied in this way comprised 20.0% by weight of $V_2O_5$, 0.4% by weight of P after calcination at 400° C. for 4 hours. The BET surface area was 24.8 $m^2/g$.

A.5 Production of the Comparative Catalyst System 5 as Described in WO 2004/103944 (Catalyst 2) (4-Zone Catalyst System)

Upper Zone (1)

29.27 g of anatase ($TiO_2$-1, BET SA: 9 $m^2/g$, $H_2$ uptake: 0.4 μmol/$m^2$), 69.80 g of anatase ($TiO_2$-2, BET SA: 20 $m^2/g$, $H_2$ uptake: 1.5 μmol/$m^2$), 7.83 g of vanadium pentoxide, 2.61 g of antimony oxide, 0.49 g of cesium carbonate were suspended in 650 ml of deionized water and stirred for 18 hours to achieve homogeneous dispersion. 50 g of organic binder comprising a copolymer of vinyl acetate and vinyl laurate in the form of a 50% strength by weight aqueous dispersion were added to this suspension. The resulting suspension was subsequently sprayed onto 1200 g of steatite (magnesium silicate) in the form of rings (7×7×4 mm, (ED)×(L)×(ID)) and dried. The weight of the shell applied was 8% of the total weight of the finished catalyst. The catalytically active composition applied in this way, i.e. the catalyst shell, comprised 7.12% by weight of vanadium (calculated as $V_2O_5$), 2.37% by weight of antimony (calculated as $Sb_2O_3$), 0.36% by weight of cesium (calculated as Cs), 27.20% by weight of titanium dioxide $TiO_2$-1) and 63.46% by weight of titanium dioxide ($TiO_2$-2) after calcination at 450° C. for one hour.

Middle Zone (b1)

24.61 g of anatase ($TiO_2$-1, BET SA: 9 $m^2$/g, $H_2$ uptake: 0.4 μmol/$m^2$), 74.46 g of anatase ($TiO_2$-2, BET SA: 20 $m^2$/g, $H_2$ uptake: 1.5 μmol/$m^2$), 7.82 g of vanadium pentoxide, 2.60 g of antimony oxide, 0.35 g of cesium carbonate were suspended in 650 ml of deionized water and stirred for 18 hours to achieve homogeneous dispersion. 50 g of organic binder comprising a copolymer of vinyl acetate and vinyl laurate in the form of a 50% strength by weight aqueous dispersion were added to this suspension. The suspension obtained was subsequently sprayed onto 1200 g of steatite (magnesium silicate) in the form of rings (7×7×4 mm, (ED)×(L)×(ID)) and dried. The weight of the shell applied was 8% of the total weight of the finished catalyst. The catalytically active composition applied in this way, i.e. the catalyst shell, comprised 7.12% by weight of vanadium (calculated as $V_2O_5$), 2.37% by weight of antimony (calculated as $Sb_2O_3$), 0.26% by weight of cesium (calculated as Cs), 22.60% by weight of titanium dioxide ($TiO_2$-1) and 67.79% by weight of titanium dioxide ($TiO_2$-2) after calcination at 450° C. for one hour.

Middle Zone (b2)

24.82 g of anatase ($TiO_2$-1, BET SA: 9 $m^2$/g, $H_2$ uptake: 0.4 μmol/$m^2$), 74.46 g of anatase ($TiO_2$-2, BET SA: 20 $m^2$/g, $H_2$ uptake: 1.5 μmol/$m^2$), 7.82 g of vanadium pentoxide, 2.60 g of antimony oxide, 0.135 g of cesium carbonate were suspended in 650 ml of deionized water and stirred for 18 hours to achieve homogeneous dispersion. 50 g of organic binder comprising a copolymer of vinyl acetate and vinyl laurate in the form of a 50% strength by weight aqueous dispersion were added to this suspension. The suspension obtained was subsequently sprayed onto 1200 g of steatite (magnesium silicate) in the form of rings (7×7×4 mm, (ED)×(L)×(ID)) and dried. The weight of the shell applied was 8% of the total weight of the finished catalyst. The catalytically active composition applied in this way, i.e. the catalyst shell, comprised 7.12% by weight of vanadium (calculated as $V_2O_5$), 2.37% by weight of antimony (calculated as $Sb_2O_3$), 0.10% by weight of cesium (calculated as Cs), 22.60% by weight of titanium dioxide ($TiO_2$-1) and 67.79% by weight of titanium dioxide ($TiO_2$-2) after calcination at 450° C. for one hour.

Bottom Zone (c)

17.23 g of anatase ($TiO_2$-1, BET SA; 9 $m^2$/g, $H_2$ uptake: 0.4 μmol/$m^2$), 69.09 g of anatase ($TiO_2$-3, BET SA: 27 $m^2$/g, $H_2$ uptake: 2.8 μmol/$m^2$), 21.97 g of vanadium pentoxide, 1.55 g of ammonium dihydrogen phosphate were suspended in 650 ml of deionized water and stirred for 18 hours to achieve homogeneous dispersion. 50 g of organic binder comprising a copolymer of vinyl acetate and vinyl laurate in the form of a 50% strength by weight aqueous dispersion were added to this suspension. The suspension obtained was subsequently sprayed onto 1200 g of steatite (magnesium silicate) in the form of rings (7×7×4 mm, (ED)×(L)×(ID)) and dried. The weight of the shell applied was 8% of the total weight of the finished catalyst. The catalytically active composition applied in this way, i.e. the catalyst shell, comprised 20.0% by weight of vanadium (calculated as $V_2O_5$), 0.38% by weight of phosphorus (calculated as P), 15.73% by weight of titanium dioxide ($TiO_2$-1) and 62.90% by weight of titanium dioxide ($TiO_2$-3) after calcination at 450° C. for one hour.

B Measurement of the Hydrogen Consumption in the Reduction of $Ti^{4+}$ to $Ti^{3+}$ 200 mg of the $TiO_2$ in the anatase modification were positioned as a powder bed in the reactor. A pretreatment to remove adsorbed water was carried out first. For this purpose, the sample was heated in helium at 20 K/min to 673 K and maintained at this temperature for one hour. After cooling to below 232 K and flushing with helium, the experiment was carried out. The sample was, for this purpose, heated at a ramp of 15 K/min to a final temperature of 1373 K in a stream of $H_2$/He (10% of $H_2$ in He, flow: 30 standard ml/min). The hydrogen consumption was determined by means of gas chromatography (thermal conductivity detector) and subsequently normalized to the amount used/surface area of the sample.

C Oxidation of o-xylene to Phthalic Anhydride

C.1 3-Zone Catalyst

From the bottom upward, 0.70 m of the catalyst of the bottom zone (c), 0.60 m of the catalyst of the middle zone (b) and 1.50 m of the catalyst of the upper zone (a) were introduced into an iron tube having a length of 3.85 m and an internal diameter of 25 mm. To regulate the temperature, the iron tube was surrounded by a salt melt, and a 2 mm thermocouple sheath having an installed withdrawable element was provided for measurement of the catalyst temperature. 4 standard $m^3$/h of air laden with from 0 to 100 g/standard $m^3$ of 98.5% strength by weight o-xylene were passed through the tube from the top downward. At 60-100 g of o-xylene/standard $m^3$, the results summarized in table 2 were obtained ("PA yield" is the amount of PA obtained in percent by weight, based on 100% pure o-xylene).

C.2 4-Zone Catalyst

From the bottom upward, 0.70 m of the catalyst of the bottom zone (c), 0.70 m of the catalyst of the middle zone 2 (b2), 0.50 m of the catalyst of the middle zone 1 (b1) and 1.30 m of the catalyst of the upper zone (a) were introduced into an iron tube having a length of 3.85 m and an internal diameter of 25- mm. Otherwise, the experiment was carried out as indicated in C.1.

The experimental results after activation are summarized in table 1.

The following abbreviations were used:

| | |
|---|---|
| HST | Hot Spot Temperature |
| UZ | Upper Zone |
| SBT | Salt Bath Temperature |
| PHD | Phthalide |
| PA | Phthalic Anhydride |

TABLE 1

Results of the catalytic tests of the 4-zone catalysts

|  | Catalyst system 1 | Catalyst system 1 | Comparative catalyst system 5 |
|---|---|---|---|
| Bed lengths [cm] | 130, 50, 70, 70 | 130, 50, 70, 70 | 130, 50, 70, 70 |
| o-Xylene loading [g/standard m³] | 80 | 100 | 100 |
| SBT [° C.] | 365 | 362 | 360 |
| HST UZ [° C.] | 439 | 447 | 440 |
| PHD [% by weight] | 0.03 | 0.03 | 0.02 |
| PA yield [% by weight] | 114.6 | 114.1 | 113.5 |

TABLE 2

Results of the catalytic tests of the 3-zone catalysts

|  | Catalyst system 2 | Comparative catalyst system 3 | Comparative catalyst system 4 |
|---|---|---|---|
| Bed lengths [cm] | 150, 70, 60 | 150, 60, 70 | 140, 80, 60 |
| o-Xylene loading [g/standard m³] | 70 | 70 | 60 |
| SBT [° C.] | 360 | 356 | 375 |
| HST UZ [° C.] | 438 | 461 | 433 |
| PHD [% by weight] | 0.02 | 0.03 | 0.05 |
| PA yield [% by weight] | 113.5 | 111.5 | 112 |

What is claimed is:

1. A process for preparing a catalyst material, the process comprising:
   (a) providing a first anatase titanium dioxide having a BET surface area greater than 15 m²/g and a hydrogen uptake for the reduction of $Ti^{4+}$ to $Ti^{3+}$ of from 5 to 20 μmol/m²;
   (b) providing a second anatase titanium dioxide having a BET surface area less than or equal to 15 m²/g, which is different than the surface area of the first anatase titanium dioxide, and a hydrogen uptake for the reduction of $Ti^{4+}$ to $Ti^{3+}$ of from 0.6 to 7 μmol/m²; and
   (c) admixing the first anatase titanium dioxide with the second anatase titanium dioxide to form a titanium dioxide mixture;
   wherein the hydrogen uptake of the first anatase titanium dioxide and the second anatase titanium dioxide are determined by measuring hydrogen consumption of an amount of a sample of each of the first anatase titanium dioxide and the second anatase titanium dioxide by gas chromatography and normalizing hydrogen consumption to the amount and surface area of each sample.

2. The process according to claim 1, wherein the first anatase titanium dioxide has a BET surface area of 18 to 90 m²/g.

3. The process according to claim 2, wherein the first anatase titanium dioxide has a hydrogen uptake for the reduction of $Ti^{4+}$ to $Ti^{3+}$ of from 5 to 17 μmol/m².

4. The process according to claim 3, wherein the second anatase titanium dioxide has a BET surface area of 3 to 15 m²/g and a hydrogen uptake for the reduction of $Ti^{4+}$ to $Ti^{3+}$ of from 0.6 to 5 μmol/m².

5. The process according to claim 4, wherein the first anatase titanium dioxide and the second anatase titanium dioxide are admixed in a ratio of 0.5:1 to 6:1.

6. The process according to claim 1, wherein the first anatase titanium dioxide has a hydrogen uptake for the reduction of $Ti^{4+}$ to $Ti^{3+}$ of from 5 to 17 μmol/m².

7. The process according to claim 1, wherein the second anatase titanium dioxide has a BET surface area of 3 to 15 m²/g.

8. The process according to claim 7, wherein the second anatase titanium dioxide has a hydrogen uptake for the reduction of $Ti^{4+}$ to $Ti^{3+}$ of from 0.6 to 5 μmol/m².

9. The process according to claim 1, wherein the second anatase titanium dioxide has a hydrogen uptake for the reduction of $Ti^{4+}$ to $Ti^{3+}$ of from 0.6 to 5 μmol/m².

10. The process according to claim 1, wherein the first anatase titanium dioxide and the second anatase titanium dioxide are admixed in a ratio of 0.5:1 to 6:1.

11. A catalytic titanium dioxide mixture comprising: a first anatase titanium dioxide having a BET surface area greater than 15 m²/g and a hydrogen uptake for the reduction of $Ti^{4+}$ to $Ti^{3+}$ of from 5 to 20 μmol/m²; and a second anatase titanium dioxide having a BET surface area less than or equal to 15 m²/g, which is different than the surface area of the first anatase titanium dioxide, and a hydrogen uptake for the reduction of $Ti^{4+}$ to $Ti^{3+}$ of from 0.6 to 7 μmol/m²;
   wherein the hydrogen uptake of the first anatase titanium dioxide and the second anatase titanium dioxide are determined by measuring hydrogen consumption of an amount of a sample of each of the first anatase titanium dioxide and the second anatase titanium dioxide by gas chromatography and normalizing hydrogen consumption to the amount and surface area of each sample.

12. The catalytic titanium dioxide mixture according to claim 11, wherein the first anatase titanium dioxide and the second anatase titanium dioxide are present in a ratio of 0.5:1 to 6:1.

13. A catalyst comprising an active composition on a support material, wherein the active composition is present in an amount of 5 to 15% by weight, based on the catalyst, and wherein the active composition comprises 3 to 30% by weight of $V_2O_5$, 0 to 4% by weight of $Sb_2O_3$, 0 to 1.0% by weight of P, 0 to 1.5% by weight of alkali, calculated as alkali metal, and a catalytic titanium dioxide mixture according to claim 11.

14. The catalyst according to claim 13, wherein the first anatase titanium dioxide and the second anatase titanium dioxide are present in a ratio of 0.5:1 to 6:1.

15. A catalyst system comprising two or more superposed catalyst zones, wherein an uppermost of the superposed catalyst zones comprises a catalyst according to claim 14.

16. A catalyst system comprising two or more superposed catalyst zones, wherein an uppermost of the superposed catalyst zones comprises a catalyst according to claim 13.

17. A process comprising: (a) providing a compound selected from the group consisting of xylene, naphthalene and mixtures thereof; and (b) subjecting the compound to gas phase oxidation with a gas comprising molecular oxygen in the presence of a catalyst system according to claim 16.

18. A process comprising: (a) providing a compound selected from the group consisting of xylene, naphthalene and mixtures thereof; and (b) subjecting the compound to gas phase oxidation with a gas comprising molecular oxygen in the presence of a catalyst according to claim 13.

19. A catalyst system comprising at least three superposed catalyst zones;
   wherein an uppermost zone of the at least three catalyst zones nearest a reactor inlet comprises a first catalyst comprising an active composition on a support material, wherein the active composition is present in an amount of 7 to 10% by weight, based on the first catalyst, and wherein the active composition comprises 6 to 11% by weight of $V_2O_5$, 0 to 3% by weight of $Sb_2O_3$, 0.1 to 1% by weight of alkali, calculated as alkali metal, and, as balance to 100% by weight, a catalytic titanium dioxide mixture according to claim 11;

wherein a next lower zone of the at least three catalyst zones comprises a second catalyst comprising an active composition on a support material, wherein the active composition is present in an amount of 7 to 12% by weight, based on the second catalyst, and wherein the active composition comprises 5 to 13% by weight of $V_2O_5$, 0 to 3% by weight of $Sb_2O_3$, 0 to 0.4% by weight of P, 0 to 0.4% by weight of alkali, calculated as alkali metal, and an anatase titanium dioxide, as balance;

and wherein a lowest zone of the at least three catalyst zones nearest a reactor outlet comprises a third catalyst comprising an active composition on a support material, wherein the active composition is present in an amount of 8 to 12% by weight, based on the third catalyst, and wherein the active composition comprises 5 to 30% by weight of $V_2O_5$, 0 to 3% by weight of $Sb_2O_3$, 0.05 to 0.4% by weight of P, 0 to 0.3% by weight of alkali, calculated as alkali metal, and an anatase titanium dioxide, as balance.

20. The catalyst system according to claim 19, wherein the next lower zone comprises two catalyst subzones, wherein the upper subzone of the two catalyst subzones comprises an upper subzone catalyst comprising an active composition on a support material, wherein the active composition is present in an amount of 7 to 12% by weight, based on the upper subzone catalyst, and wherein the active composition comprises 4 to 15% by weight of $V_2O_5$, 0 to 3% by weight of $Sb_2O_3$, 0.1 to 1% by weight of alkali, calculated as alkali metal, 0 to 0.4% by weight of P, and an anatase titanium dioxide, as balance; and wherein the lower subzone of the two catalyst subzones comprises a lower subzone catalyst comprising an active composition on a support material, wherein the active composition is present in an amount of 7 to 12% by weight, based on the lower subzone catalyst, and wherein the active composition comprises 5 to 15% by weight of $V_2O_5$, 0 to 3% by weight of $Sb_2O_3$, 0 to 0.4% by weight of alkali, calculated as alkali metal, 0 to 0.4% by weight of P, and an anatase titanium dioxide, as balance.

* * * * *